(12) United States Patent
Buisine et al.

(10) Patent No.: US 8,633,336 B2
(45) Date of Patent: Jan. 21, 2014

(54) METHOD FOR SEPARATING A CARBOXYLIC ACID IN SALIFIED FORM BEARING AT LEAST ONE HALOGEN ATOM

(75) Inventors: Olivier Buisine, Saint Genis Laval (FR); François Metz, Irigny (FR)

(73) Assignee: Rhodia Operations, Aubervilliers (FR)

( * ) Notice: Subject to any disclaimer, the term of this patent is extended or adjusted under 35 U.S.C. 154(b) by 297 days.

(21) Appl. No.: 13/003,136

(22) PCT Filed: Jul. 8, 2009

(86) PCT No.: PCT/EP2009/058688
§ 371 (c)(1),
(2), (4) Date: Mar. 23, 2011

(87) PCT Pub. No.: WO2010/003986
PCT Pub. Date: Jan. 14, 2010

(65) Prior Publication Data
US 2011/0166385 A1 Jul. 7, 2011

(30) Foreign Application Priority Data
Jul. 10, 2008 (FR) ...................................... 08 03932

(51) Int. Cl.
*C07C 53/21* (2006.01)
(52) U.S. Cl.
USPC .......................................................... 562/605
(58) Field of Classification Search
None
See application file for complete search history.

(56) References Cited

U.S. PATENT DOCUMENTS 6,281,374 B1 8/2001 Schultz

FOREIGN PATENT DOCUMENTS

WO WO 0035834 6/2000

OTHER PUBLICATIONS

Database Caplus Chemical Abstracts Service, Columbus, Ohio, US; Database Accession No. 1998:771358, Abstract of Jung et al., DE 19747790, Nov. 26, 1998.*

* cited by examiner

*Primary Examiner* — Karl J Puttlitz
(74) *Attorney, Agent, or Firm* — Hunton & Williams LLP

(57) ABSTRACT

The subject of the present invention is a method for separating a carboxylic acid in salified form bearing at least one halogen atom at the α position of the carbonyl group from a medium comprising it. The method according to the invention, for separating a carboxylic acid in salified form bearing at least one halogen atom at the α position of the carbonyl group from an aqueous medium comprising it, is characterized by the fact that the latter is brought into contact with an onium salt leading to the formation of two phases: an organic phase comprising the salt resulting from the reaction of the salt of the carboxylic acid bearing at least one halogen atom at the α position of the carbonyl group and of the onium salt leading to the displacement of the cation from the carboxylic acid by the onium, an aqueous phase comprising the various salts, in particular the one resulting from the reaction of the cation of the carboxylic acid with the anion of the onium, and by the fact that the organic and aqueous phases are then separated and that the onium salt of the carboxylic acid is recovered from the organic phase.

19 Claims, No Drawings

METHOD FOR SEPARATING A CARBOXYLIC ACID IN SALIFIED FORM BEARING AT LEAST ONE HALOGEN ATOM

CROSS-REFERENCE TO RELATED APPLICATIONS

This application is the U.S. National Phase of International Application No. PCT/EP2009/058688 filed on Jul. 8, 2009, which claims priority to French Application No. FR 08 03932 filed Jul. 10, 2008, both of which are incorporated by reference herein in their entireties.

FIELD OF THE INVENTION

One subject of the present invention is a process for separating a carboxylic acid in salified form bearing at least one halogen atom at the α position of the carbonyl group from a medium comprising it.

More precisely, the invention relates to the separation of a carboxylic acid in salified form bearing at least one fluorine atom at the α position of the carbonyl group.

The invention more particularly targets the separation of difluorocarboxylic and perfluorocarboxylic acids in salified form from synthesis media comprising them.

BACKGROUND

There are various methods for preparing difluoro-carboxylic and perfluorocarboxylic acids.

Fluorinated derivatives of aliphatic nature, that is to say the fluorinated derivatives in which the fluorine is borne, at least partly, by an $sp^3$ carbon, are generally obtained by an exchange of a halogen atom with a fluorine atom. This exchange generally takes place using hydrofluoric acid or else salts of hydrofluoric acid.

Another preparation process described in EP-A 1 137 615 lies in a selective hydrodehalogenation process which consists in substituting a halogen atom heavier than fluorine with a hydrogen atom.

This process is defined in that it comprises a step of hydrogenation of a substrate comprising a carbon atom of $sp^3$ hybridization bearing an electron-attracting group and at least one fluorine atom and a halogen atom heavier then fluorine, in a basic aqueous medium and in the presence of a group VIII metal, preferably Raney nickel.

By way of examples, it is stated that sodium difluoroacetate is obtained with an excellent yield of greater than 90% by hydrogenation under pressure, from chlorodifluoroacetic acid, in sodic solution and in the presence of Raney nickel.

Thus, at the end of the reaction, an aqueous medium is obtained that comprises the sodium salt of difluoroacetic acid, sodium chloride formed during the reaction and an excess of sodium hydroxide.

The problem that is faced is that it is difficult to separate the sodium salt of the difluoroacetic acid formed during the reaction since it is a water-soluble product which is in the presence of other salts in the medium which makes the separation by filtration impossible.

Generally, the conventional technique used by a person skilled in the art is to separate said acid by an acidification followed by an extraction which involves using an organic solvent in which said acid is soluble. The difficulty is in identifying solvents that allow the solubilization and extraction of the acid from an aqueous phase.

To overcome this drawback, the present invention proposes a process that makes it possible to get round the aforementioned drawbacks.

SUMMARY OF THE INVENTION

A process has now been found, and it is this which constitutes the subject of the present invention, for separating a carboxylic acid in salified form bearing at least one halogen atom at the α position of the carbonyl group from an aqueous medium comprising it, characterized by the fact that the latter is brought into contact with an onium salt leading to the formation of two phases:

an organic phase comprising the salt resulting from the reaction of the carboxylic acid salt bearing at least one halogen atom at the α position of the carbonyl group and of the onium salt leading to the displacement of the cation of the carboxylic acid by the onium, an aqueous phase comprising the various salts in particular the one resulting from the reaction of the cation of the carboxylic acid with the anion of the onium, and by the fact that the organic and aqueous phases are then separated and the onium salt of the carboxylic acid is recovered from the organic phase.

DETAILED DESCRIPTION OF PREFERRED EMBODIMENTS

In the present text, the onium salt of the carboxylic acid is also known by the term "complex".

According to one variant of the process of the invention, the organic phase may be diluted with a solvent in which it is soluble and the onium salt of the carboxylic acid is recovered from said organic phase.

In order to illustrate the process of the invention and without any limiting character, the Applicant cites the case of the sodium salt of difluoroacetic acid which is obtained as previously mentioned in a medium comprising sodium chloride and an excess of sodium hydroxide.

In accordance with the process of the invention, the medium obtained is brought into contact with an onium salt and more preferably with the tetra(n-butyl)-ammonium hydrogensulfate resulting in the following reaction:

The reaction scheme of the process of the invention is given below in order to facilitate the understanding of the invention without however binding the scope of the invention to this process.

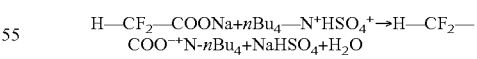

H—CF$_2$—COONa+$n$Bu$_4$—N$^+$HSO$_4^+$→H—CF$_2$—COO$^-$+N-$n$Bu$_4$+NaHSO$_4$+H$_2$O

The organic phase comprising H—CF$_2$—COO$^-$ $^+$N-n Bu$_4$ may be separated from the aqueous phase.

The invention applies to any acid organic compound comprising at least one carboxylate anion present in an aqueous medium, in the presence of other salts resulting from the preparation process thereof.

Thus, the invention also targets monoacids, diacids or mixtures of acids.

The substrates more particularly concerned by the present invention correspond to the following formula:

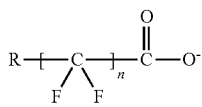

(I)

in said formula:
n is a number between 0 and 10,
if n is equal to 0, R represents an $R_1R_2CF$ group of formula (II) in which $R_1$ and $R_2$ represent a hydrogen atom, or a fluorine, chlorine or bromine atom,
if n is different from 0, R represents a hydrogen atom, a fluorine, chlorine or bromine atom or a carboxylate function.

The substrates used preferably correspond to the formula (I) in which n is equal to 0 and R represents a group of formula (II).

More preferably still, the substrates correspond to the formula (I) in which n is equal to 0 and R represents an $R_2R_2CF$ group of formula (II) in which $R_1$ and $R_2$ represent a hydrogen atom and/or a fluorine atom.

As examples of substrates, mention may be made of the salts of monocarboxylic and dicarboxylic acids, alone or as a mixture:
fluoroacetic acid,
difluoroacetic acid, DFA,
trifluoroacetic acid, TFA,
chlorodifluoroacetic acid, CDFA,
bromodifluoroacetic acid,
perfluoropropanoic acid,
perfluorobutanoic acid,
perfluoroheptanoic acid,
perfluorooctanoic acid,
perfluorodecanoic acid,
tetrafluorosuccinic acid,
hexafluoroglutaric acid.

The invention applies more particularly to the salts of DFA or TFA acids or to mixtures thereof.

In the process of the invention, the carboxylic acids are in salified form, preferably in the form of an alkali metal salt, preferably the sodium or potassium salt.

In accordance with the process of the invention, the salt of said carboxylic acid or acids is brought into contact in the presence of an onium salt.

The onium salts capable of being used in the process of the invention are those in which the onium ions derive, in particular, from nitrogen, phosphorus, sulfur, oxygen, carbon or iodine, coordinated to hydrocarbon-based residues. The onium ions that derive from nitrogen or phosphorus will be four-coordinated, the onium ions that derive from sulfur, oxygen, carbon or S=O will be three-coordinated whereas the onium ions that derive from iodine will be two-coordinated.

The hydrocarbon-based residues coordinated to these various elements are optionally substituted alkyl, alkenyl, aryl, cycloalkyl or aralkyl groups, it being possible for two coordinated hydrocarbon-based residues to together form a single divalent group.

The nature of the anions bonded to these organic cations is not of critical importance. All "hard" or "intermediate" bases are suitable as the anion.

The expression "hard" or "intermediate" base is understood to mean any anion corresponding to the conventional definition given by R. Pearson in Journal of Chem. Ed. 45, pages 581-587 (1968), the terms "hard" and "intermediate" respectively having the meaning of the terms "hard" and "borderline" used in this reference.

Among the onium ions which may be used in the present process of the invention, those corresponding to one of the following general formulae are particularly suitable:

(III)

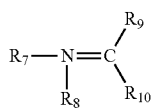

(IV)

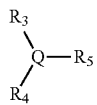

(V)

in said formulae:
W represents N or P,
Q represents S, S=O or C,
$R_3$, $R_4$, $R_5$ and $R_6$, which are identical or different, represent:
  a linear or branched alkyl group having 1 to 16 carbon atoms and optionally substituted with one or more of the following groups or atoms: phenyl, hydroxyl, halogen, nitro, alkoxy or alkoxycarbonyl, the alkoxy groups having 1 to 4 carbon atoms;
  a linear or branched alkenyl group having 2 to 12 carbon atoms;
  an aryl group having 6 to 10 carbon atoms, optionally substituted with one or more of the following groups or atoms: alkyl having 1 to 4 carbon atoms, alkoxy, alkoxycarbonyl, the alkoxy group having 1 to 4 carbon atoms, or halogen;
  two of said $R_3$ to $R_6$ groups possibly together forming a linear or branched alkylene, alkenylene or alkadienylene group having 3 to 6 carbon atoms;
$R_7$, $R_8$, $R_9$, $R_{10}$ are identical or different and represent:
  a hydrogen atom,
  a linear or branched alkyl group containing from 1 to 6 carbon atoms;
  the $R_9$ and $R_{10}$ groups possibly together forming an alkylene group containing from 3 to 6 carbon atoms;
  the $R_8$ and $R_9$ or $R_8$ and $R_{10}$ groups possibly together forming an alkylene, alkenylene or alkadienylene group containing 3 or 4 carbon atoms and constituting, with the nitrogen atom, a nitrogen-containing heterocycle optionally substituted as mentioned above and it being possible for one of the carbon atoms to optionally be replaced with a nitrogen atom optionally bearing an $R_{11}$ group which is a linear or branched alkyl group containing from 1 to 20 carbon atoms.

Among the oniums of formula (III) those which are preferred correspond to the formula (III) in which W is a nitrogen or phosphorus atom and $R_3$, $R_4$, $R_5$ and $R_6$, which are identical or different, represent a linear or branched alkyl group having 1 to 12 carbon atoms and a benzyl group.

Among the oniums of formula (IV), those which are preferred correspond to one of the following formulae:

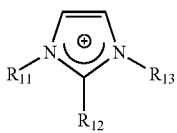

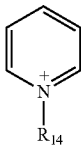

in said formulae:
the $R_{11}$ group represents an alkyl group having from 1 to 20 carbon atoms,
the $R_{12}$ group represents a hydrogen atom, or an alkyl group having from 1 to 4 carbon atoms,
the $R_{13}$ group represents an alkyl group having from 1 to 4 carbon atoms,
the $R_{14}$ group represents an alkyl group having from 1 to 6 carbon atoms.

Among the "hard" or "intermediate" bases which may constitute the anion of said onium salts, mention may be made of the ions: $F^-$, $ClO_4^-$, $PF_5^-$, $BF_{4-}$, $PO_4^{3-}$, $HPO_4^{2-}$, $H_2PO_4^-$, $CH_3SO_3^-$, $Ph\text{-}SO_3^-$, $CH_3Ph\text{-}SO_3^-$, $HSO_4^-$, $SO_4^{2-}$, $NO_3^-$, $AlCl_{4-}$, $Cl^-$, $Br^-$, $I^-$, $OH^-$, Ph representing a phenyl group, and also all the other anions corresponding to the definition of "hard" or "intermediate" bases by Pearson.

For reasons of ease of use, said anions could be chosen from: bromide, chloride, hydrogensulfate or hydrogenphosphate.

As examples of onium ions corresponding to formula (III), mention made of the following cations:
tetramethylammonium,
triethylmethylammonium
tributylmethylammonium,
trimethylpropylammonium,
tetraethylammonium,
tetrabutylammonium,
dodecyltrimethylammonium,
methyltrioctylammonium,
heptyltributylammonium,
tetrapropylammonium,
tetrapentylammonium,
tetrahexylammonium,
tetraheptylammonium,
tetraoctylammonium,
tetradecylammonium,
butyltripropylammonium,
methylributylammonium,
pentyltributylammonium,
methyldiethylpropylammonium,
ethyldimethylpropylammonium,
tetradodecylammonium,
tetraoctadecylammonium,
hexedecyltrimethylammonium,
benzyltrimethylammonium,
benzyldimethylpropylammonium,
benzyldimethyloctylammonium,
benzyltributylammonium,
benzyltriethylammonium,
phenyltrimethylammonium,
benzyldimethyltetradecylammonium,
benzyldimethylhexadecylammonium,
dimethyldiphenylammonium,
methyltriphenylammonium,
buten-2-yltriethylammonium,
N,N-dimethyltetramethyleneammonium,
N,N-diethyltetramethyleneammonium,
tetramethylphosphonium,
tetrabutylpihosphonium,
ethyltrimethylphosphonium,
trimethylpentylphosphonium,
octyltrimethylphosphonium,
dodecyltrimethylphosphonium,
trimethylphenylphosohonium,
diethyldimethylphosphonium,
dicyclohexyldimethylphosphonium,
dimethyldiphenylphosphonium,
cyclohexyltrimethylphosphonium,
triethylmethylphosphonium,
methyltri(isopropyl)phosphonium,
methyltri(n-propyl)phosphonium,
methyltri(isobutyl)phosphonium,
methyltri(n-butyl)phosohonium,
diisobutyl(n-octyl)methylphosphonium,
methyltri(2-methylpropyl)phosphonium,
methyltricylohexylphosphonium,
methyltriphenylphosphonium,
methyltribenzylphosphonium,
methyltri(4-methylphenyl)phosphonium,
methyltrixylylphosphonium,
diethylmethylphenylphosphonium,
dibenzylmethylphenylphosphonium,
ethyltriphenylphosphonium,
tetraethylphosphonium,
ethyltri(n-propyl)phosphonium,
triethylpentylphosphonium,
hexadecyltributylphosphonium
ethyltriphenylphosphonium,
n-butyltri(n-propyl)phosphonium,
butyltriphenylphosphonium,
benzyltriphenylphosphonium,
(β-phenylethyl)dimethylphenylphosphonium,
tetraphenylphosphonium,
triphenyl(4-methylphenyl)phosphonium,
tetrakis(hydroxymethyl)phosphonium.

Among the cations corresponding to the formula (IV), mention may be made of the following cations:
1-alkyl-2,3-dimethylimidazoliums,
1-alkyl-3-methylimidazoliums,
1-alkylpyridiniums,
N-methylpicolinium.

As examples of onium ions corresponding to the formula (V), mention may be made of the following cations:
trimethylsulfonium,
triethylsulfonium,
triphenylsulfonium,
trimethylsulfoxonium,
triphenylcarbenium.

Among the onium ions which may be used within the context of the present process, quaternary ammonium ions, quaternary phosphonium ions and imidazolinium and pyridinium ions will usually be preferred.

As more specific examples of onium salts, mention may be made of the 1-alkyl-2,3-dimethylimidazolium salts such as 1-ethyl-2,3-dimethylimidazolium, 1-butyl-2,3-dimethylimidazolium or 1-hexyl-2,3-dimethylimidazolium bromide; 1-ethyl-2,3-dimethylimidazolium, 1-butyl-2,3-dimethylimidazolium or 1-hexyl-2,3-dimethylimidazolium chloride; 1-butyl-2,3-dimethylimidazolium or 1-hexyl-2,3-dimethylimidazolium tetrafluoroborate; the 1-alkyl-3-methylimidazolium salts such as 1-ethyl-3-methylimidazolium or 1-hexyl-3-methylimidazolium bromide; 1-ethyl-3-methylimidazolium, 1-butyl-3-methylimidazolium, 1-hexyl-3-methylimidazolium, 1-octyl-3-methylimidazolium, 1-decyl-3-methylimidazolium, 1-dodecyl-3-methylimidazolium, 1-tetradecyl-3-methylimidazolium, 1-hexadecyl-3-methylimidazolium, or 1-octadecyl-3-methylimidazolium chloride; 1-butyl-3-methylimidazolium, 1-hexyl-3-methylimidazolium or 1-octyl-3-methylimidazolium hexafluorophosphate; 1-butyl-3-methylimidazolium or 1-hexyl-3-methylimidazolium tetrafluoroborate; the 1-alkylpyridinium salts such as 1-ethylpyridinium, 1-butylpyridinium or 1-hexylpyridinium bromide; 1-ethylpyridinium or 1-butylpyridinium chloride; 1-hexylpyridinium chloride; 1-butylpyridinium or 1-hexylpyridinium hexafluorophosphate; and 1-butylpyridinium or 1-hexylpyridinium tetrafluoroborate.

However, it is very particularly preferred to use the bromide, chloride, hydrogensulfate or hydrogenphosphate of tetrabutylammonium, methyltri(n-butyl)ammonium, N-methyl-N,N,N-trioctylammonium, trimethylphenylphosphonium, tetrabutylphosphonium, methyltri(n-butyl)-phosphonium, methyltri(isobutyl)phosphonium or diisobutyl-n-octylmethylphosphonium.

The onium salt may be introduced during the process of the invention, in the solid state or in the form of a solution in one of its solvents, usually water.

The substrate is brought into contact with the onium salt.

The amount of onium salt used is generally at least equal to the stoichiometric amount. Thus, it is such that the molar ratio between said onium salt and the acid substrate varies between 1 and 5, preferably between 1.2 and 1.5. The upper limit is not critical and may be greatly exceeded without any drawback since the catalyst may optionally be recycled at the end of the reaction.

As mentioned previously, the reaction is carried out in an aqueous medium advantageously in the absence of any organic solvent.

According to one preferred embodiment of the invention, a concentration of the acid substrate is chosen that is as high as possible depending on its solubility.

Generally, the concentration of the acid substrate in aqueous solution varies between 5 and 40% by weight and preferably lies between 10 and 20% by weight.

The reaction is advantageously carried out according to the "one-pot" principle, the order for the introduction of the reactants not being critical.

The temperature at which the process of the invention is carried out is generally between 10° C. and 60° C., preferably at ambient temperature. The expression "ambient temperature" is understood to mean a temperature that usually lies between 15° C. and 25° C.

From a practical viewpoint, the aqueous solution of the substrate and the onium salt which may be in liquid or solid form are mixed with stirring.

According to one variant of the process of the invention, it is possible to add an organic solvent in which the final onium salt is soluble.

As examples, mention may be made of halogenated or unhalogenated, aliphatic, cycloaliphatic or aromatic hydrocarbons and more particularly toluene, dichloro-methane and dichlorobenzene.

The amount of solvent introduced generally represents half of the volume of the aqueous phase.

The mixture is brought to the chosen temperature.

At the end of the reaction, a two-phase liquid medium is obtained that comprises an organic phase comprising the complex resulting from the reaction of the carboxylic acid salt bearing at least one halogen atom at the α position of the carbonyl group and of the onium salt leading to the displacement of the cation of the carboxylic acid by the onium and an aqueous phase comprising the various salts in particular the one resulting from the reaction of the cation of the carboxylic acid with the anion of the onium.

The complex obtained is present in the organic phase which may be separated from the aqueous phase, especially by decantation.

The acid function of the complex obtained in the organic phase is released by treatment using an acid such as, for example, hydrochloric, sulfuric, sulfonic or nitric acid.

An amount of acid generally ranging from stoichiometry up to an excess, for example of 20%, is used.

Said acid is recovered from the organic phase, according to the techniques conventionally used such as, for example, distillation or extraction using a suitable solvent such as for example an ester, ethyl or butyl acetate; an alcohol such as butanol or octanol; a halogenated aliphatic hydrocarbon such as dichloro-methane or dichloroethane.

One advantage of the invention is the separation selectivity of the fluorinated species with respect to the non-fluorinated species.

The process of the invention makes it possible to treat mixtures comprising monofluorinated, difluorinated or polyfluorinated compounds, in particular aqueous effluents comprising said fluorinated compounds: the most fluorinated compound always being extracted preferentially.

Given below are exemplary embodiments of the invention given by way of indication and with no limiting character.

In the examples, the term "RR" defines the ratio between the number of moles extracted in the organic phase and the number of moles initially introduced into the aqueous phase.

EXAMPLES 1 TO 5

Added to 10 g of an aqueous solution containing 1.6 g of sodium difluoroacetate, 0.2 g of sodium trifluoro-acetate and 0.9 g of sodium chloride are 22.4 mmol of onium salt mentioned in table (I), i.e. 1.5 equivalents with respect to the total sum of difluoroaceate and trifluoroacetate salts.

The whole mixture is left stirring for 30 minutes then is left to settle.

The upper organic phase is recovered by decantation.

The extraction yields (RR) of the difluoroacetic (DFA) and trifluoroacetic (TFA) acid salts, expressed by the ratio between the number of moles extracted in the organic phase and the number of moles initially introduced into the aqueous phase, are summarized in the table below:

TABLE I

| Ref. Ex. | Onium nature | % DFA extracted | % TFA extracted |
|---|---|---|---|
| 1 | Aliquat 336 N-Methyl-N,N,N-trioctylammonium chloride | 64.5 | 99.6 |
| 2 | Tetrabutylammonium bromide | 65.5 | 99.8 |
| 3 | Tetrabutylphosphonium chloride | 36.2 | 97.5 |
| 4 | Methyltributylammonium chloride | 83.6 | 85.5 |
| 5 | Tetrabutylammonium hydrogensulfate | 99.5 | 100.0 |

EXAMPLE 6

Added to 80 g of an aqueous solution containing 13 g of sodium difluoroacetate and 1.8 g of sodium trifluoro-acetate are 67.2 g of tetrabutylammonium hydrogen-sulfate.

The whole mixture is left for 10 hours, with stirring, at ambient temperature.

The phases are then decanted and separated.

51 g of aqueous phase and 87 g of organic phase are obtained.

All of the fluorinated species are found in the organic phase (RR=100%).

This organic phase is brought to 74° C. under a pressure of 60 mbar until all the water has been distilled.

After returning to atmospheric pressure, 26 g of sulfuric acid are added, and the whole mixture is put under a reduced pressure of 60 mbar and the temperature is gradually raised from 54° C. up to 120° C.

7.2 g of distillate containing 5.7 g of difluoroacetic acid are obtained, i.e. a yield expressed by the ratio between the number of moles of difluoroacetic acid obtained and the number of moles of sodium difluoroacetate introduced, of 54%.

EXAMPLE 7

Potassium trifluoroacetate (9.7 g; 63.8 mmol), tetrabutylammonium bromide (43.4 g; 128 mmol) are charged to a reactor, in the presence of water (75 g) and dichloromethane (65 g).

The whole mixture is stirred at ambient temperature and the phases are decanted.

The organic phase obtained contains 88% of the trifluoroacetate anions initially introduced (RR).

The invention claimed is:

1. A process for separating a carboxylic acid of formula (I),

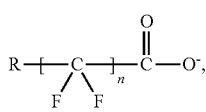
(I)

from an aqueous medium, comprising:
contacting a carboxylic acid of formula (I) in salified form with an onium salt to form two phases:
(i) an organic phase comprising a carboxylic acid anion of said carboxylic acid in salified form and a cation of the onium salt, and
(ii) an aqueous phase comprising a cation of said carboxylic acid in salified form and an anion of the onium salt,
separating the organic phase and the aqueous phase, and recovering the carboxylic acid from the organic phase,
wherein said process is carried in the absence of any organic solvent, and in said formula (I):
n is a number ranging from 0 to 10:
if n is equal to 0, then R represents an $R_1R_2CF$ group wherein $R_1$ and $R_2$ independently represent a hydrogen, fluorine, chlorine, or bromine atom;
if n is not 0, then R represents a hydrogen, fluorine, chlorine, or bromine atom or a carboxylate function.

2. The process of claim 1, wherein the carboxylic acid is:
fluoroacetic acid,
difluoroacetic acid,
trifluoroacetic acid,
chlorodifluoroacetic acid,
bromodifluoroacetic acid,
perfluoropropanoic acid,
perfluorobutanoic acid,
perfluoroheptanoic acid,
perfluorooctanoic acid,
perfluorodecanoic acid,
tetrafluorosuccinic acid,
hexafluoroglutaric acid, or
a mixture thereof.

3. The process of claim 1, wherein the salt of the carboxylic acid comprises an alkali metal salt.

4. The process of claim 1, wherein the carboxylic acid salt comprises an alkali metal salt of difluoroacetic acid, trifluoroacetic acid, or a mixture thereof.

5. The process of claim 1, wherein the onium salt comprises an onium corresponding to formula:

(III)

(IV)

(V)

wherein:
W represents N or P;
Q represents S, S=O or C;
$R_3$, $R_4$, $R_5$ and $R_6$, which are identical or different, represent:
a linear or branched alkyl group having from 1 to 16 carbon atoms, optionally substituted with one or more of the following groups or atoms: phenyl, hydroxyl, halogen, nitro, alkoxy or alkoxycarbonyl,
wherein the alkoxy groups have from 1 to 4 carbon atoms;
a linear or branched alkenyl group having from 2 to 12 carbon atoms; or
an aryl group having from 6 to 10 carbon atoms, optionally substituted with one or more of the following groups or atoms: alkyl having 1 to 4 carbon atoms, alkoxy, alkoxycarbonyl, or halogen;
wherein the alkoxy groups have from 1 to 4 carbon atoms; and
$R_7$, $R_8$, $R_9$, and $R_{10}$ which are identical or different, represent:
a hydrogen atom, or
a linear or branched alkyl group having from 1 to 6 carbon atoms.

6. The process of claim 5, wherein two of said groups $R_3$, $R_4$, $R_5$ and $R_6$ together form a linear or branched alkylene, alkenylene or alkadienylene group having from 3 to 6 carbon atoms.

7. The process of claim 1, wherein the onium salt comprises an onium corresponding to formula:

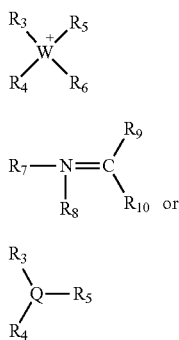

(III)

(IV)

(V)

wherein:
W represents N or P;
Q represents S, S=O or C;
$R_3$, $R_4$, $R_5$ and $R_6$, which are identical or different, represent:
a linear or branched alkyl group having from 1 to 16 carbon atoms, optionally substituted with one or more of the following groups or atoms: phenyl, hydroxyl, halogen, nitro, alkoxy or alkoxycarbonyl,
wherein the alkoxy groups have from 1 to 4 carbon atoms;
a linear or branched alkenyl group having from 2 to 12 carbon atoms; or
an aryl group having from 6 to 10 carbon atoms, optionally substituted with one or more of the following groups or atoms: alkyl having 1 to 4 carbon atoms, alkoxy, alkoxycarbonyl, or halogen;
wherein the alkoxy groups have from 1 to 4 carbon atoms;
$R_7$ and $R_8$, which are identical or different, represent:
a hydrogen atom, or
a linear or branched alkyl group having from 1 to 6 carbon atoms; and
$R_9$ and $R_{10}$ groups together form an alkylene group having from 3 to 6 carbon atoms.

8. The process of claim 1, wherein the onium salt comprises an onium corresponding to formula:

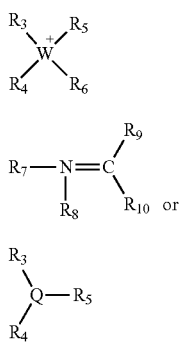

(III)

(IV)

(V)

wherein:
W represents N or P;
Q represents S, S=O or C;
$R_3$, $R_4$, $R_5$ and $R_6$, which are identical or different, represent:
a linear or branched alkyl group having from 1 to 16 carbon atoms, optionally substituted with one or more of the following groups or atoms: phenyl, hydroxyl, halogen, nitro, alkoxy or alkoxycarbonyl,
wherein the alkoxy groups have from 1 to 4 carbon atoms;
a linear or branched alkenyl group having from 2 to 12 carbon atoms; or
an aryl group having from 6 to 10 carbon atoms, optionally substituted with one or more of the following groups or atoms: alkyl having 1 to 4 carbon atoms, alkoxy, alkoxycarbonyl, or halogen;
wherein the alkoxy groups have from 1 to 4 carbon atoms; and
$R_7$, $R_9$, and $R_{10}$ which are identical or different, represent:
a hydrogen atom, or
a linear or branched alkyl group having from 1 to 6 carbon atoms;
provided that the $R_8$ and $R_9$ groups or the $R_9$ and $R_{10}$ groups together form an alkylene, alkenylene or alkadienylene group having 3 or 4 carbon atoms and comprise, together with the nitrogen atom, an optionally-substituted-nitrogen-comprising heterocycle.

9. The process of claim 8, wherein one of the carbon atoms on the optionally-substituted-nitrogen-comprising heterocycle comprises a nitrogen atom optionally bearing a linear or branched alkyl group having from 1 to 20 carbon atoms.

10. The process of claim 1, wherein the onium comprises an ammonium, phosphonium, imidazolinium or pyridinium ion.

11. The process of claim 1, wherein the anion of the onium salt comprises sulfate, hydrogensulfate, hydrogenphosphate, bromide, or chloride.

12. The process of claim 1, wherein the onium salt comprises a bromide, chloride, hydrogensulfate, or hydrogenphosphate of tetrabutylammonium, methyltri-(n-butyl)ammonium, N-methyl-N,N,N-trioctylammonium, trimethylphenylphosphonium, tetrabutylphosphonium, methyltri(n-butyl)phosphonium, methyltri(isobutyl)phosphonium or diisobutyl-noctylmethylphosphonium.

13. The process of claim 1, wherein the molar ratio of the onium salt to the carboxylic acid ranges from 1 to 5.

14. The process of claim 1, wherein the reaction is carried out at a temperature ranging from 10° C. to 60° C.

15. The process of claim 1, further comprising mixing an aqueous solution of the carboxylic acid in salified form and the onium salt by stirring,
wherein the onium salt is in liquid or solid form.

16. The process of claim 1, wherein said separating step comprises separating a complex present in the organic phase by decantation.

17. The process of claim 1, wherein said recovering step comprises recovering the carboxylic acid from the organic phase by treatment with an acid.

18. The process of claim 1, wherein the carboxylic acid is recovered from the organic phase by distillation or extraction with a solvent.

19. The process of claim 1, comprising recovering a monofluorinated, difluorinated, or polyfluorinated compound.

* * * * *

UNITED STATES PATENT AND TRADEMARK OFFICE
CERTIFICATE OF CORRECTION

PATENT NO.        : 8,633,336 B2                                           Page 1 of 1
APPLICATION NO. : 13/003136
DATED             : January 21, 2014
INVENTOR(S)       : Buisine et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 371 days.

Signed and Sealed this
Twenty-second Day of September, 2015

Michelle K. Lee
*Director of the United States Patent and Trademark Office*